United States Patent [19]
Mixon

[11] Patent Number: 5,993,839
[45] Date of Patent: Nov. 30, 1999

[54] ANTIMICROBIAL GLOVES AND A METHOD OF MANUFACTURE THEREOF

[75] Inventor: Grover C. Mixon, Kingstree, S.C.

[73] Assignee: Phoenix Medical Technology, Inc., Andrews, S.C.

[21] Appl. No.: 09/060,053

[22] Filed: Apr. 15, 1998

Related U.S. Application Data

[60] Continuation-in-part of application No. 08/782,755, Jan. 10, 1997, Pat. No. 5,906,823, which is a division of application No. 08/239,880, May 9, 1994, Pat. No. 5,725,867.

[51] Int. Cl.$^6$ .............................. A61K 7/00; A01N 25/34

[52] U.S. Cl. ........................................ 424/402; 424/404

[58] Field of Search ..................................... 424/402, 404; 2/168

[56] References Cited

U.S. PATENT DOCUMENTS

| | | | |
|---|---|---|---|
| 5,031,245 | 7/1991 | Milner | 2/168 |
| 5,725,867 | 3/1998 | Mixon | 424/402 |

*Primary Examiner*—Thurman K. Page
*Assistant Examiner*—Sharon Howard
*Attorney, Agent, or Firm*—Rogers & Killeen

[57] ABSTRACT

Antimicrobial protection may be provided to protective gloves by mixing an antimicrobial agent in a glove material film so that the antimicrobial agent migrates to the exposed surfaces of the gloves when the agent on the glove surface has been depleted. Antimicrobial gloves suitable for use in the food industry may be manufactured using heat sealing/cutting of an extruded film that includes by weight percentages: polymer resin (such as polyethylene) 96 to 98.4%, ethylene vinyl acetate resin 1.0 to 2.0%, antistatic agent (such as polyethylene glycol) 0.3 to 1.0%, and triclosan 0.3 to 1.0%.

38 Claims, No Drawings

ANTIMICROBIAL GLOVES AND A METHOD OF MANUFACTURE THEREOF

This is a continuation-in-part application of application Ser. No. 08/782,755 filed Jan. 10, 1997, now U.S. Pat. No. 5,906,823 which is a divisional of application Ser. No. 08/239,880 filed May 9, 1994 (U.S. Pat. No. 5,725,867).

BACKGROUND OF THE INVENTION

The present invention relates to sanitary food-handling gloves and a method of manufacturing such gloves, and more particularly to food-handling gloves that prevent microbial transfer and methods for making such gloves.

The food industry has long been concerned about bacterial contamination to consumers through the handling of food by food industry workers. Workers in the food industry are frequently required to wear gloves to reduce the likelihood that the bacteria from their hands is transferred to consumers. However, even gloves may pick up contaminating bacteria from food or work surfaces, thereby significantly reducing the effectiveness of the gloves the longer they are worn. A solution, albeit a costly one, is to have the workers change or disinfect their gloves frequently. The food industry would prefer a more workable and cost effective solution.

The food industry generally uses gloves made of polyvinyl chloride (PVC), polyethylene (PE), and Acrylonitrile-butadeine (Nitrile). These gloves must meet federal standards for thickness, strength, elasticity, deformation, etc. Gloves of other materials have been tried, but they either do not meet the federal standards or are not acceptable to the food industry (e.g., high cost, weak seams, difficult to don and remove, uncomfortable to wear, etc.).

In handling food using disposable gloves, it is desirable to provide continued bacterial protection during extended glove use. Despite this need, the food industry has been unable to find an antimicrobial agent that meets federal standards for food handling, that is useable with inexpensive disposable gloves, and that effectively reduces the risk of bacterial contamination during prolonged wear of the gloves. For example, conventional PVC gloves may be dusted with an antimicrobial agent, but the agent would not be effective for prolonged periods because it would rub off during use and disappear completely when the gloves are immersed in water.

For the retail food industry, where food products are handled shortly before being served to consumers, distributing a releasable chemical, such as an antimicrobial agent, in food-handling gloves for providing bacterial protection is not suggested by the prior art and is contrary to accepted wisdom. For example, when the glove is in use, the chemical is released from the glove to other surfaces including the food under preparation; thereby the chemical becomes an additive to the food being prepared for serving. This chemical additive may affect the taste of the food, may cause allergic reactions, may cause a negative psychological response (i.e., opposition or repulsion to the addition of an antimicrobial chemical to the food), may cause health concerns about eating nonorganic foods, and may cause negative health consequences to consumers due to the cumulative or long term consumption of the chemical. Further, antimicrobial agents are generally not known to be edible.

Accordingly, the prior art has focused primarily on antimicrobial solutions in the medical field. For example, U.S. Pat. No. 5,091,442 issued Feb. 25, 1992 to Milner suggests that an antimicrobial agent, such as triclosan, may be mixed with a natural rubber latex plastisol to provide antimicrobial protection for a tubular article such as a condom or catheter. However, the effectiveness of the antimicrobial agent in the article will still diminish during use because the agent will gradually disappear from the surface of the article and will not be replenished. That is, the triclosan will be removed from the surface of the natural rubber latex long before the latex wears down to expose the triclosan in the interior thereof. The nature of the natural rubber latex prevents the antimicrobial agent from migrating to the exposed surface of the latex from its interior. This limitation may be acceptable where the article makes a single contaminating contact, but is not acceptable for gloves that will have numerous contacts with diverse potential contaminants.

The Milner patent mentions that PVC may be used instead of the natural rubber latex, but does not suggest how this is to be done. The method disclosed relates only to natural rubber latex, and the differences between latex and PVC preclude the application of the disclosed method to PVC.

It has also been suggested that an antimicrobial agent may be added to a plastic or polymeric film material, such as PE, that is used to make a surgical drape sheet. The structure of the PE allows some antimicrobial agents to migrate to the exposed surface of the drape from the interior thereof when the agent has been removed from the surface (see U.S. Pat. No. 5,069,907 issued Dec. 3, 1991 to Mixon, et al.). However, the process and apparatus used therewith does not suggest adding an antimicrobial agent to plastic or polymeric film gloves for food handling. Antimicrobial agents are generally not known to be safe for oral consumption.

Additionally, food-handling gloves and medical drapes (Mixon, et al.) operate differently and are manufactured to meet different industry and federal requirements. For example, both the process of manufacture and the physical characteristics of the medical drape are directed at providing high puncture resistance.

Mixon, et al. also discloses a method of manufacturing plastic or polymeric sheets through extrusion of a thin film. Forming gloves by heat cutting two layers of extruded film is well known in the art. However, despite the low cost of manufacturing gloves through the extrusion-heat cutting technique and the long felt need for improved microbial protection of food consumers from food contamination, the food industry has not produced a low cost disposable glove having extended antimicrobial qualities.

Accordingly, it is an object of the present invention to provide novel gloves and a method of making gloves that obviate the problems of the prior art.

It is another object of the present invention to provide novel microbial transfer prevention gloves and a method of providing microbial transfer prevention to such gloves in which an antimicrobial agent in the glove material migrates to the exposed surfaces of the gloves when the agent at the glove surface has been depleted.

It is still another object of the present invention to provide a novel method of making food-handling gloves in which an antimicrobial agent is mixed in a polyethylene film before the gloves are formed by a heat cutting process whereby the antimicrobial agent migrates to the exposed surfaces of the gloves when the antimicrobial agent at the surface has been depleted.

These and many other objects and advantages of the present invention will be readily apparent to one skilled in the art to which the invention pertains from a perusal of the claims, the appended drawings, and the following detailed description of preferred embodiments.

DESCRIPTION OF PREFERRED EMBODIMENTS

Antimicrobial protection may be provided to consumers with protective gloves by mixing an antimicrobial agent with the glove material before manufacturing the glove, the agent and material being selected so that the antimicrobial agent migrates to the exposed surfaces of the gloves when the agent at the glove surface has been depleted.

The antimicrobial agent is preferably triclosan and the glove material preferably includes a polymer, such as PVC, polyethylene (PE), or nitrile. The glove material preferably includes 96 to 98.4% polymer by weight and 0.3 to 1.0% triclosan by weight.

Triclosan (2,4,4'-trichloro-2'-hydroxydiphenyl ether) is a broad spectrum antimicrobial agent that is commercially available under the name Microban™ (Clinitex Corp.) and is suitable for use in the food industry.

Antimicrobial gloves suitable for use in the food industry may be manufactured using a heat cutting process with a material that includes the following weight percentages of (a) a polyethylene resin, 96 to 98.4%, (b) ethylene vinyl acetate (EVA) resin, 1.0 to 2.0%, (c) an antistatic agent (such as polyethylene glycol), 0.3 to 1.0%, and (d) triclosan, 0.3 to 1.0%.

The antistatic agent may be any suitable product that has been approved for use in the food industry, such as polyethylene glycol.

In a preferred embodiment, the glove material includes 97.5% PE resin (weight percentage), 1.5% EVA resin, 0.7% antistatic agent, and 0.3% triclosan.

The gloves may be formed using a conventional heat cutting process, such as described in *Plastics Engineering Handbook,* page 784–786 (Society of the Plastics Industry, Inc., 1976). The process is also known as heat bonding or heat seal stamping. Initially, a film is formed by a film blowing extrusion technique. A blow film type extruder having a circular die is used to produce a film having a thickness of less than 76.1 microns (0.003 inches) and greater than 38.1 microns (0.0015 inches). Preferably, the thickness is 63.5 microns (0.0025 inches) to 76.2 microns (0.003 inches). This technique involves extrusion of polymeric compound fed through the circular die, followed by expansion, cooling, and collapsing of the blown bubble. In operation, the blown film is extruded through guiding devices into a set of pinch rolls which flatten it. The gloves are formed by heat cutting and thereby bonding two films of the glove material with a high speed roller/cutter. Where, the preferred speed setting of the roller/cutter is selected based on the type of film material being used, the required seam strength of the glove, and the thickness of the film.

In a preferred embodiment the polymer is polyethylene (PE). A conventional heat cutting process for manufacturing gloves provides an inexpensive and high volume method of manufacturing PE gloves having an antimicrobial agent throughout. The heat cutting process with PE as the polymer results in a glove which meets industry requirements in a cost effective way.

The gloves provide effective antimicrobial protection, meeting all applicable federal regulations. During use, as the antimicrobial agent at the surface of the material wears off, the agent in the material migrates to the surface to provide continued protection.

While preferred embodiments of the present invention have been described, it is to be understood that the embodiments described are illustrative only and the scope of the invention is to be defined solely by the appended claims when accorded a full range of equivalence, many variations and modifications naturally occurring to those skilled in the art from a perusal hereof.

What is claimed is:

1. A microbial transfer prevention glove for preventing food contamination during food preparation, the glove comprising an antimicrobial agent homogeneously distributed in a material from which the glove is formed, said antimicrobial agent provides an antimicrobial effect, said antimicrobial effect being depleted through the transfer of the antimicrobial agent from the glove surface to other surfaces during the glove's use, said antimicrobial effect being renewed through the migration of the antimicrobial agent from the interior of the glove material to the glove surface when the antimicrobial effect is depleted.

2. The glove of claim 1, wherein the glove material comprises polyethylene.

3. The glove of claim 1, wherein the antibacterial agent is triclosan.

4. The glove of claim 1, wherein the glove material comprising by weight percentage:
   polyethylene, 96 to 98.4%;
   ethylene vinyl acetate, 1 to 2%;
   antistatic agent, 0.3 to 1.0%; and
   triclosan, 0.3 to 1.0%.

5. The glove of claim 4, wherein the glove material comprising by weight percentage:
   polyethylene, 97.5%;
   ethylene vinyl acetate, 1.5%;
   antistatic agent, 0.7%; and
   triclosan, 0.3 to 1.0%.

6. An antimicrobial glove having an antimicrobial agent homogeneously distributed in a material from which the glove is formed, and in which the agent migrates to the exposed surface of the glove to restore the antimicrobial effect when the agent at the exposed surface has been removed, the glove material comprising by weight percentage:
   polyethylene, 96 to 98.4%;
   ethylene vinyl acetate, 1 to 2%;
   antistatic agent, 0.3 to 1.0%; and
   triclosan, 0.3 to 1.0%,
   wherein said triclosan internal to the glove material will migrate to the surface of the glove when said triclosan at the surface of the glove is removed.

7. The glove of claim 6 wherein the weight percentages are:
   said polyethylene, 97.5%;
   said ethyl vinyl acetate, 1.5%;
   said antistatic agent, 0.7%; and
   said triclosan, 0.3%.

8. A method of providing microbial protection to consumers of prepared foods, comprising the steps of:
   (a) providing a glove having an antimicrobial agent distributed through the material of the glove;
   (b) preparing food for consumption; and
   (c) releasing the antimicrobial agent from the glove for an extended period.

9. The method of claim 8, wherein the material of the glove comprises polyethylene.

10. The method of claim 8, wherein the antimicrobial agent is triclosan.

11. The method of claim 10, wherein the glove material comprises 0.3 to 1.0% triclosan by weight.

12. The method of claim 8, wherein the antimicrobial agent in the glove material migrates to glove surfaces as the antimicrobial agent being released from glove surfaces.

13. The method of claim 8, wherein the step of preparing food and the step of releasing antimicrobial agent are performed simultaneously.

14. A method of manufacturing antimicrobial gloves for food handling, the gloves having an antimicrobial agent homogeneously distributed in a material from which the gloves are formed, and in which the agent migrates to the exposed surface of the glove to restore the antimicrobial effect when the agent at the exposed surface has been removed, the method comprising the steps of:

(a) mixing granules of a polymer and an antimicrobial agent;

(b) forming a film from said granules; and (e) cutting using heat two layers of the film to provide the antimicrobial gloves, wherein the antimicrobial agent internal to the glove migrates to the surface of the glove when the antimicrobial agent at the surface of the glove is removed.

15. The method of claim 14 wherein the material comprises:
polyethylene, 96–98.4%,
ethylene vinyl acetate, 1.0 to 2.0%,
polyethylene glycol, 0.3 to 1.0%, and
triclosan, 0.3 to 1.0%.

16. The method of claim 15 wherein the material comprises:
polyethylene, 97.5%,
ethylene vinyl acetate, 1.5%,
polyethylene glycol, 0.7%, and
triclosan, 0.3%.

17. A method of providing microbial transfer prevention to the surfaces of a food-handling glove during extended use, comprising the steps of distributing an antimicrobial agent throughout the glove material and handling foods with the glove.

18. The method of claim 17, wherein during the step of handling foods, the antimicrobial agent migrates away from the surface of the glove and migrates from the interior of the glove material to the surface of the glove.

19. The method of claim 17, wherein the antimicrobial agent is triclosan.

20. The glove of claim 17, wherein the glove comprises by weight percentage:
polyethylene, 96 to 98.4%;
ethylene vinyl acetate, 1 to 2%;
antistatic agent, 0.3 to 1.0%; and
triclosan, 0.3 to 1.0%.

21. The glove of claim 20, wherein the glove comprises by weight percentage:
polyethylene, 97.5%;
ethylene vinyl acetate, 1.5%;
antistatic agent, 0.7%; and
triclosan, 0.3 to 1.0%.

22. A food-handling glove for use in the preparation of food, the glove comprising a mixture of a polymer and an antimicrobial agent formed into a food-handling glove, the antimicrobial agent being gradually released from the glove during extended glove use.

23. The glove of claim 22, wherein the polymer is polyethylene.

24. The glove of claim 22, wherein the antimicrobial agent is triclosan.

25. The glove of claim 22, wherein the mixture comprises by weight percentage:
polyethylene, 96 to 98.4%;
ethylene vinyl acetate, 1 to 2%;
antistatic agent, 0.3 to 1.0%; and
triclosan, 0.3 to 1.0%.

26. The glove of claim 25, wherein the mixture comprises by weight percentage:
said polyethylene, 97.5%;
said ethyl vinyl acetate, 1.5%;
said antistatic agent, 0.7%; and
said triclosan, 0.3%.

27. A polymer apparatus for use in food-handling, the apparatus having a thin polymer film for separating food from unsterilized surfaces during food-handling, the improvement comprising an antimicrobial agent composite with the thin polymer film, said agent being released as a disinfectant from the surfaces of the film over an extended period of use.

28. The apparatus of claim 27, wherein the polymer is polyethylene.

29. The apparatus of claim 27, wherein the antimicrobial agent is triclosan.

30. The apparatus of claim 27, wherein the apparatus comprises by weight percentage:
polyethylene, 96 to 98.4%;
ethylene vinyl acetate, 1 to 2%;
antistatic agent, 0.3 to 1.0%; and
triclosan, 0.3 to 1.0%.

31. The apparatus of claim 30, wherein the apparatus comprising by weight percentage:
said polyethylene, 97.5%;
said ethyl vinyl acetate, 1.5%;
said antistatic agent, 0.7%; and
said triclosan, 0.3%.

32. A food packaging and preparation glove comprising a polymer film and an agent distributed throughout said film, said agent being antimicrobial, and said agent being gradually released from the surface of the polymer film when the glove is in use.

33. The glove of claim 32, wherein the polymer is polyethylene.

34. The glove of claim 32, wherein the agent is triclosan.

35. The glove of claim 32, wherein the glove comprises by weight percentage:
polyethylene, 96 to 98.4%;
ethylene vinyl acetate, 1 to 2%;
antistatic agent, 0.3 to 1.0%; and
triclosan, 0.3 to 1.0%.

36. The glove of claim 35, wherein the apparatus comprises by weight percentage:
said polyethylene, 97.5%;
said ethyl vinyl acetate, 1.5%;
said antistatic agent, 0.7%; and
said triclosan, 0.3%.

37. A microbial transfer prevention system for food handling, comprising a glove formed from a polymer material, an antimicrobial agent dispersed throughout the material, the antimicrobial agent on the surface of the glove being transferred away from the glove during glove contact with other surfaces including food surfaces, the antimicrobial agent in the interior of the material migrating to the surface of the material as the agent on the surface of the glove is transferred away from the surface of the glove during use.

38. The system of claim 37, wherein the agent is triclosan.

* * * * *